United States Patent [19]

Grohe

[11] Patent Number: 4,611,080

[45] Date of Patent: Sep. 9, 1986

[54] PREPARATION OF HALOGENATED AROYLACETIC ACID ESTERS

[75] Inventor: Klaus Grohe, Odenthal, Fed. Rep. of Germany

[73] Assignee: Bayer Aktiengesellschaft, Leverkusen, Fed. Rep. of Germany

[21] Appl. No.: 754,692

[22] Filed: Jul. 12, 1985

[30] Foreign Application Priority Data

Jul. 18, 1984 [DE] Fed. Rep. of Germany ....... 3426482

[51] Int. Cl.⁴ .............................................. C07C 69/76
[52] U.S. Cl. .................................... 560/51; 568/323; 568/331
[58] Field of Search .......................................... 560/51

[56] References Cited

U.S. PATENT DOCUMENTS 2,848,459 8/1958 Pribyl et al. ........................... 560/51
3,818,072 6/1974 Grisar et al. ........................... 560/51

FOREIGN PATENT DOCUMENTS 2536977 3/1977 Fed. Rep. of Germany .
2537047 3/1977 Fed. Rep. of Germany .
106290 8/1980 Poland .

OTHER PUBLICATIONS

Denzel, T., et al., Arch. Pharm. (Weinheim Ger.) 309(6), 486–503, 1976.
Mikslajczyk, J. et al., Pr. Inst. Przem. Org. 5, 71–97, 1973.
Prudchenko, A. T. et al., Zh. Obshch. Khim 37(11) 2487–93, 1967.
Filler, R. et al., J. Org. Chim. 35(4) 930–5 1970.
Osadchii, S. A. et al., Zh. Org. Khim 6(8) 1627–36, 1970.
Vlasov, V. M. et al., Zh Org Khim 13(11) 2372–81, 1977.
Taylor, Ed. C. et al., Org. Prep. Proced. Inst. 10(5) 221–4, 1978.

Primary Examiner—Paul J. Killos
Attorney, Agent, or Firm—Sprung, Horn, Kramer & Woods

[57] ABSTRACT

A process for the preparation of a halogenated aroylacetic acid ester of the formula

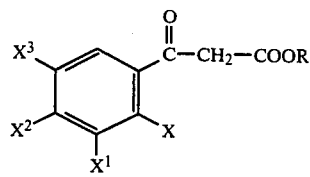

in which R is alkyl with 1–6 carbon atoms, X and $X^2$ each independently is halogen, and $X^1$ and $X^3$ each independently is hydrogen or halogen, comprising reacting a benzoyl chloride of the formula

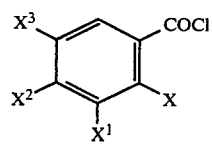

with dichloroethylene in the presence of anhydrous aluminum chloride to form the corresponding benzene trichloroethyl ketone, dehydrochlorinating the trichloroethyl ketone to form the corresponding benzene dichlorovinyl ketone, and treating the dichlorovinyl ketone with an alcoholate and then with an aqueous acid. The products are known intermediates for known antibacterials.

10 Claims, No Drawings

PREPARATION OF HALOGENATED AROYLACETIC ACID ESTERS

The present invention relates to a process for the preparation of halogenated aroylacetic acid esters, which are useful intermediates for the synthesis of highly active antibacterial medicaments.

It has been found that halogenated aroylacetic acid esters of the formula I

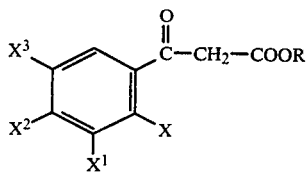

in which
R represents alkyl with 1–6 carbon atoms,
X represents halogen, preferably chlorine or fluorine,
$X^1$ denotes hydrogen or halogen, preferably fluorine,
$X^2$ can be halogen, preferably chlorine or fluorine, and
$X^3$ represents hydrogen or halogen, preferably fluorine, are obtained when benzoyl chlorides of the formula II in which X, $X^1$, $X^2$ and $X^3$ have the abovementioned meaning, are reacted with dichloroethylene III in the presence of anhydrous aluminum chloride to give the aryl trichloroethyl ketones IV, these are converted into the aryl dichlorovinyl ketones V by splitting off of hydrogen chloride and the ketones are treated with an alcoholate and then with an aqueous acid.

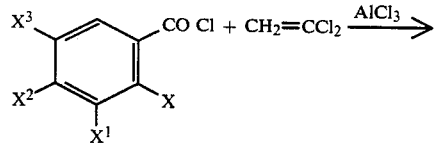

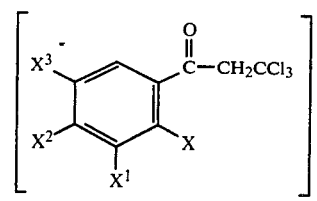

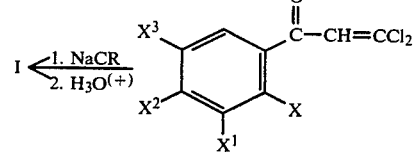

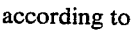

The process according to the invention has a number of advantages. Thus, purification of the ketones IV can be dispensed with and the crude products can be dehydrochlorinated to V directly by means of heat, if appropriate in the presence of catalytic amounts of triphenylphosphine, or with stoichiometric amounts of triethylamine. V is then purified by distillation under a high vacuum.

It has already been disclosed that aroylacetic acid esters which are halogenated in the aroyl radical are obtained when the corresponding halogenated aroyl halides are reacted with malonic acid esters in the presence of magnesium ethylate to give the aroylmalonic acid esters and these are hydrolyzed and decarboxylated to give the aroylacetic acid esters, an alkoxycarbonyl group being selectively split off (DE-OS (German Published Specification) 3,142,854).

However, this process has a number of disadvantages. Thus, for example, acetophenone is formed to a greater or lesser degree by more extensive hydrolysis and decarboxylation.

If 2,4-dichloro-5-fluoro-benzoyl chloride (1) is used as the starting substance, the course of the reaction can be represented by the following equation:

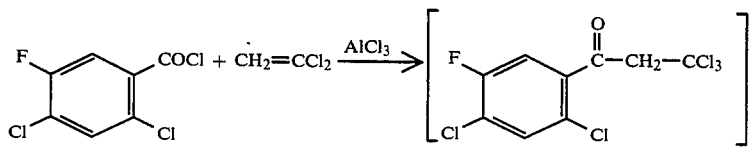

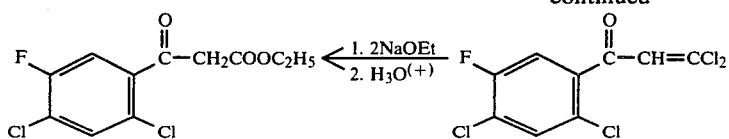 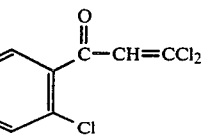

The aroylacetic acid ester (4) serves as an intermediate for the synthesis of the antibacterial broad spectrum chemotherapeutic ciprofloxacin (DE-OS (German Published Specification) 3,142,854), which is obtained by the following route:

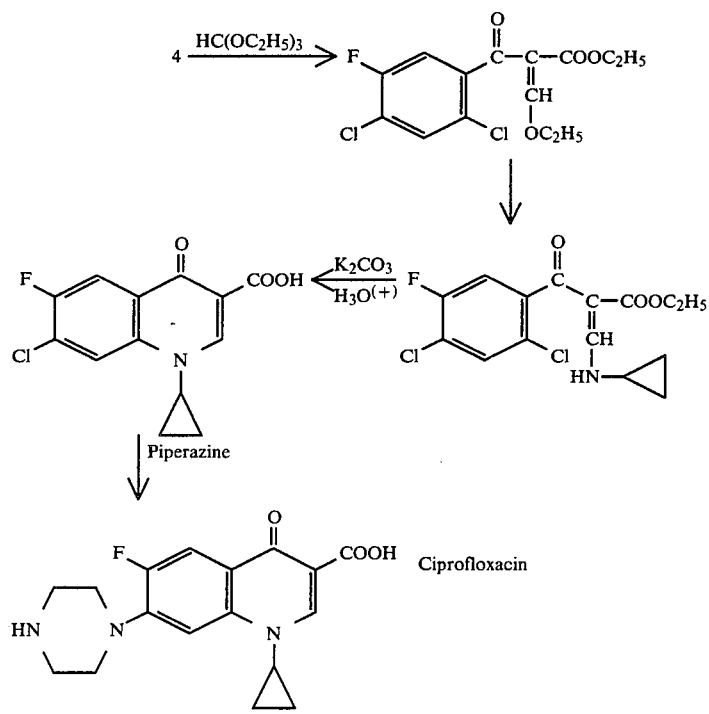

In formula (I), R preferably represents methyl or ethyl.

The fluorine- and chlorine-containing benzoyl chlorides which can be used according to the invention or the corresponding carboxylic acids or carboxylic acid fluorides are known, for example, from DE-OS (German Published Specification) 3,142,856.

Examples which may be mentioned are: 2,4-dichloro-5-fluoro-benzoyl chloride, 2,4,5-trifluorobenzoyl chloride, 2,3,4,5-tetrafluoro-benzoyl chloride, 2,4,5-trichlorobenzoyl chloride, 2,3,4,5-tetrachloro-benzoyl chloride and 2,4,5-trifluoro-3-chlorobenzoyl chloride.

The reaction of the halogenated benzoyl chlorides II with dichloroethylene III to give IV is preferably carried out in an inert diluent. Possible diluents are carbon disulphide and methylene chloride.

The reaction is carried out at temperatures between 10° and 40° C., preferably between 20° and 30° C. The reaction is preferably carried out under normal pressure.

In carrying out the process according to the invention, 1 mole of anhydrous aluminum chloride is employed per mole of carboxylic acid chloride II. An excess of 5 to 10% is advantageous.

1 mole of dichloroethylene III is required for 1 mole of benzoyl chloride II. It has proved advantageous to use 1.5 to 3 moles of dichloroethylene per mole of (II).

For the dehydrochlorination, the aryl trichloroethyl ketones IV are heated at 80° to 180° C., preferably 120° to 150° C., with catalytic amounts (about 0.1 g per 100 g of crude product) of triphenylphosphine until the evolution of gas has ended. The mixture can then be distilled directly under a high vacuum, the aryl dichlorovinyl ketones V formed being obtained in a high yield and purity.

The splitting off of HCl can also be carried out with stoichiometric amounts of a tertiary base, such as, for example, triethylamine, in a solvent, such as, for example, methylene chloride or toluene. When the reaction, which already proceeds at room temperature, has ended, the mixture is washed with water and dried with sodium sulphate and, after the solvent has been distilled off, the vinyl ketone V is purified by distillation in vacuo.

To react the aryl dichlorovinyl ketones V with an alcoholate, 2 g atoms of sodium or 2 moles of sodium alcoholate are dissolved in an anhydrous alcohol, preferably methyl alcohol or ethyl alcohol. 1 mole of dichlorovinyl ketone is then introduced, with thorough cooling. When the exothermic reaction has ended, the mixture is stirred at room temperature for about a further hour and the alcohol is removed in vacuo. The residue is taken up in methylene chloride, the mixture is shaken with dilute sulphuric acid and the aroylacetic acid ester is isolated and purified by distillation in vacuo.

EXAMPLE 1

Ethyl 2,4-dichloro-5-fluoro-benzoylacetate

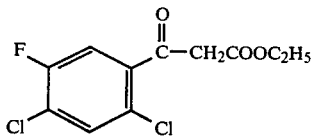

28.8 g (0.1 mole) of 2,2-dichlorovinyl 2,4-dichloro-5-fluoro-phenyl ketone are added in portions to a solution of 4.6 g of sodium in 80 ml of absolute ethanol at 0°–5° C., while cooling (ice/methanol) and stirring. When the exothermic reaction has subsided, the mixture is stirred at room temperature for a further 30 minutes, the solvent is stripped off in vacuo and the residue is taken up in 100 ml of methylene chloride. The mixture is shaken thoroughly with 100 ml of 2N sulphuric acid, the methylene chloride solution is separated off in a separating funnel and the aqueous phase is extracted another three times with 50 ml of methylene chloride each time. The combined methylene chloride solutions are washed with 100 ml of saturated sodium chloride solution and dried over sodium sulphate. The solvent is then distilled off in vacuo. The brown oily residue crystallizes on standing. Distillation under a fine vacuum gives 22.3 g (79.9%) of ethyl 2,4-dichloro-5-fluoro-benzoylacetate of boiling point 125°–126° C./0.16 mbar. Colorless crystals of melting point 44°–45° C.

The 2,2-dichlorovinyl 2,4-dichloro-5-fluorophenyl ketone used as the starting material is obtained as follows:

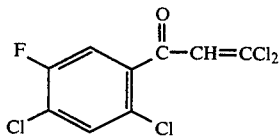

136.5 g (0.6 mole) of 2,4-dichloro-5-fluorobenzoyl chloride and 97 g (1 mole) of 1,1-dichloroethylene are successively added dropwise to a suspension of 84 g of anhydrous aluminum chloride in 300 ml of methylene chloride, while cooling with ice and stirring, during which the temperature should not exceed 30° C. The mixture is stirred at room temperature for 3 hours and poured onto a mixture of about 600 g of ice and 60 ml of concentrated hydrochloric acid, the organic phase is separated off and the aqueous phase is subsequently extracted three times with 100 ml of methylene chloride. The methylene chloride solution is washed with 100 ml of water and dried with sodium sulphate and the solvent is distilled off in vacuo. The residue (218.8 g) is heated at 130°–140° C. with 0.34 g of triphenylphosphine until the initially vigorous evolution of HCl has ended (about ¾ hour). Distillation under a fine vacuum gives 167.1 g (96.4%) of 2,2-dichlorovinyl 2,4-dichloro-5-fluorophenyl ketone of boiling point 121°–123° C./0.13 mbar, melting point 64°–65° C.

EXAMPLE 2

Methyl 2,4-dichloro-5-fluoro-benzoylacetate

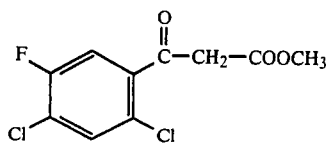

57.6 g (0.2 mole) of 2,2-dichlorovinyl 2,4-dichloro-5-fluoro-phenyl ketone are added in portions to a solution of 9.2 g of sodium in 100 ml of absolute methanol at 0°–10° C., while cooling (ice/CH₃OH) and stirring. The orange-brown suspension is stirred at room temperature for 40 minutes and the solvent is then distilled off in vacuo. The residue is taken up in about 200 ml of methylene chloride and 100 ml of 2N sulphuric acid, the mixture is shaken thoroughly, the phases are separated and the sulphuric acid solution is subsequently extracted three times with 80 ml of methylene chloride each time. The combined $CH_2Cl_2$ solutions are washed with 50 ml of saturated sodium chloride solution and dried with sodium sulphate and the methylene chloride is stripped off in vacuo. 53 g of a brown solid product of melting point 78°–83° C. are obtained. Distillation under a fine vacuum gives 48 g (90.6%) of methyl 2,4-dichloro-5-fluoro-benzoylacetate of boiling point 134°–137° C./0.15–0.17 mbar. The colorless crystals have a melting point of 77°–79° C. (Distillation residue: 4.1 g of dark brown oil which partly crystallizes). The crude product can be purified by recrystallization from light petrol/Tonsil.

EXAMPLE 3

Ethyl 2,4,5-trifluoro-benzoylacetate

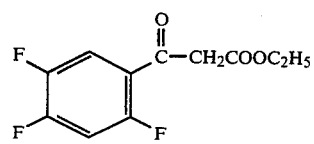

21.2 g of 2,2-dichlorovinyl 2,4,5-trifluorophenyl ketone are added dropwise to a solution of 3.85 g of sodium in 65 ml of absolute ethanol at 5°–10° C., while cooling (ice/methanol) and stirring. When the exothermic reaction has subsided, the mixture is stirred at room temperature for a further 30 minutes, the solvent is stripped off in vacuo and the residue is taken up in 100 ml of methylene chloride. The mixture is shaken thoroughly with 50 ml of 2N sulphuric acid, the methylene chloride phase is separated off in a separating funnel and the aqueous phase is subsequently extracted another three times with 50 ml of methylene chloride each time. The combined $CH_2Cl_2$ solutions are washed with 100 ml of saturated sodium chloride solution and dried over sodium sulphate. The solvent is then distilled off in vacuo and the oily residue is fractionated under a fine vacuum. 16.8 g (82.2%) of ethyl 2,4,5-trifluoro-benzoylacetate of boiling point 98°–100° C./0.15 mbar are obtained. The melting point is 63°–64° C.

The 2,2-dichlorovinyl 2,4,5-trifluorophenyl ketone used as the starting material can be obtained as follows:

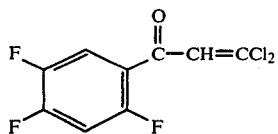

25 g of 2,4,5-trifluorobenzoyl chloride in 10 ml of methylene chloride and 37.5 g of 1,1-dichloroethylene are successively added dropwise to a suspension of 18.5 g of anhydrous aluminum chloride in 75 ml of dry methylene chloride, while cooling with ice and stirring, during which the temperature does not exceed 15° C. The mixture is stirred at about 15° C. for 2 hours, is allowed to come to room temperature overnight and is poured onto a mixture of 150 g of ice and 15 ml of concentrated hydrochloric acid, the organic phase is separated off and the aqueous phase is subsequently extracted with methylene chloride. The methylene chloride solution is washed with water and dried with sodium sulphate and the diluent is distilled off in vacuo. The residue (44 g) is heated at 130°–140° C. with 0.1 g of triphenylphosphine until the initially vigorous evolution of gas has ended (about 45 minutes). Distillation in vacuo gives 23.8 g (72.8%) of 2,2-dichlorovinyl 2,4,5-trifluorophenyl ketone of boiling point 132°–134° C./14 mbar.

It will be understood that the specification and examples are illustrative but not limitative of the present invention and that other embodiments within the spirit and scope of the invention will suggest themselves to those skilled in the art.

I claim:

1. A process for the preparation of a halogenated aroylacetic acid ester of the formula

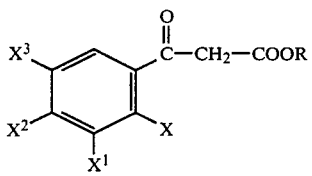

in which

R is alkyl with 1–6 carbon atoms,

X and $X^2$ each independently is halogen, and $X^1$ and $X^3$ each independently is hydrogen or halogen, comprising reacting a benzoyl chloride of the formula

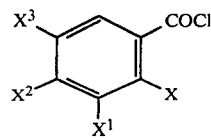

with dichloroethylene in the presence of anhydrous aluminum chloride to form the corresponding benzene trichloroethyl ketone, dehydrochlorinating the trichloroethyl ketone to form the corresponding benzene dichlorovinyl ketone, and treating the dichlorovinyl ketone with an alcoholate and then with an aqueous acid.

2. A process according to claim 1 wherein the reaction of the benzoyl chloride with dichloroethylene is carried out at a temperature of 10° to 40° C.

3. A process according to claim 1, wherein the reaction of the benzoyl chloride with dichloroethylene is carried out using 1 mole of anhydrous aluminum chloride per mole of benzoyl chloride.

4. A process acccording to claim 1, wherein the reaction of the benzoyl chloride with dichloroethylene is carried out using 1.5–3 moles of dichloroethylene per mole of benzoyl chloride.

5. A process according to claim 1, wherein the dehydrochlorination of the benzene trichloroethyl ketone is carried out in the presence of a catalytic amount of triphenylphosphine.

6. A process according to claim 5, wherein the dehydrochlorination is carried out at a temperature of 80° to 180° C.

7. A process according to claim 1, wherein the dehydrochlorination of the benzene trichloroethyl ketone is carried out in the presence of a stoichiometric amount of a tertiary base in a solvent.

8. A process according to claim 1, wherein the benzenedichlorovinyl ketone is treated with 2 moles of sodium alcoholate in anhydrous alcohol and then with dilute aqueous sulphuric acid.

9. A process according to claim 1, wherein the reaction with the benzoyl chloride is carried out in carbon disulphide or methylene chloride.

10. A process according to claim 6,
in which

X and $X^2$ each independently is chlorine or fluorine, and $X^1$ and $X^3$ each is fluorine, the reaction with the benzoyl chloride is carried out in carbon disulphide or methylene chloride at a temperature of 20° to 30° C. using 1 mole of anhydrous aluminum chloride per mole of benzoyl chloride and 1.5–3 moles of dichloroethylene per mole of benzoyl chloride, the dehydrochlorination of the benzene trichloroethyl ketone is carried out in the presence of a stoichiometric amount of a tertiary base in a solvent, and the benzenedichlorovinyl ketone is treated with 2 moles of sodium alcoholate in anhydrous alcohol and then with dilute aqueous sulphuric acid.

* * * * *